United States Patent
Shepard et al.

(10) Patent No.: US 12,213,913 B2
(45) Date of Patent: Feb. 4, 2025

(54) MEDICAL IMPLANT

(71) Applicant: ALCON INC., Fribourg (CH)

(72) Inventors: Thomas A. Shepard, Rolesville, NC (US); Tyler Pegoraro, Raleigh, NC (US); Stuart Williams, Raleigh, NC (US); Sanjib Kumar Das, Cary, NC (US); Leo Anthony Trevino, Hurdle Mills, NC (US); Cheng Li, Durham, NC (US)

(73) Assignee: ALCON INC., Fribourg (CH)

( * ) Notice: Subject to any disclaimer, the term of this patent is extended or adjusted under 35 U.S.C. 154(b) by 0 days.

(21) Appl. No.: 17/893,338

(22) Filed: Aug. 23, 2022

(65) Prior Publication Data

US 2024/0065970 A1    Feb. 29, 2024

Related U.S. Application Data

(63) Continuation of application No. 17/518,281, filed on Nov. 3, 2021.

(60) Provisional application No. 63/241,395, filed on Sep. 7, 2021, provisional application No. 63/109,615, filed on Nov. 4, 2020.

(51) Int. Cl.
```
A61F 9/00      (2006.01)
A61K 9/00      (2006.01)
B29C 33/38     (2006.01)
G03F 7/00      (2006.01)
```

(52) U.S. Cl.
CPC .......... *A61F 9/0017* (2013.01); *A61K 9/0024* (2013.01); *A61K 9/0051* (2013.01); *B29C 33/3842* (2013.01); *G03F 7/0002* (2013.01); *B29K 2867/003* (2013.01); *B29K 2883/00* (2013.01)

(58) Field of Classification Search
CPC .... A61K 9/0024; A61K 9/0051; A61F 9/0017
See application file for complete search history.

(56) References Cited

U.S. PATENT DOCUMENTS 3,630,200 A * 12/1971 Higuchi ............... A61K 9/0051
                                                        424/427
5,756,127 A *  5/1998 Grisoni ................ A61K 9/0024
                                                        424/9.4

(Continued)

FOREIGN PATENT DOCUMENTS

WO    2017015604 A1    1/2017
WO    2017210627 A1   12/2017

OTHER PUBLICATIONS

International Search Report for International Application No. PCT/US2021/057992, issued Feb. 11, 2022.

(Continued)

*Primary Examiner* — Guy K Townsend
*Assistant Examiner* — Peter Daniel Smith
(74) *Attorney, Agent, or Firm* — MCDONNELL BOEHNEN HULBERT & BERGHOFF LLP

(57) ABSTRACT

A medical implant is disclosed. The medical implant includes a body having a first end having a first cross-sectional dimension, a second end having a second cross-sectional dimension, and a tapered portion extending between the first end and the second end. The first cross-sectional dimension is larger than the second cross-sectional dimension. In some embodiments, the body comprises multiple layers.

16 Claims, 17 Drawing Sheets

(56) References Cited

U.S. PATENT DOCUMENTS

| | | | |
|---|---|---|---|
| 6,264,971 B1 | 7/2001 | Darougar et al. | |
| 10,667,947 B2 | 6/2020 | Horvath et al. | |
| 2005/0244465 A1* | 11/2005 | Nivaggioli | A61P 27/06 |
| | | | 424/427 |
| 2017/0136224 A1 | 5/2017 | Roorda et al. | |
| 2019/0358439 A1* | 11/2019 | Michal | A61M 31/007 |
| 2021/0069101 A1* | 3/2021 | Naga | A61L 27/54 |
| 2021/0353532 A1* | 11/2021 | Naga | A61L 27/58 |
| 2022/0257502 A1 | 8/2022 | Imran | |

OTHER PUBLICATIONS

International Preliminary Report on Patentability for International Application No. PCT/US2021/057992, issued May 8, 2023.

* cited by examiner

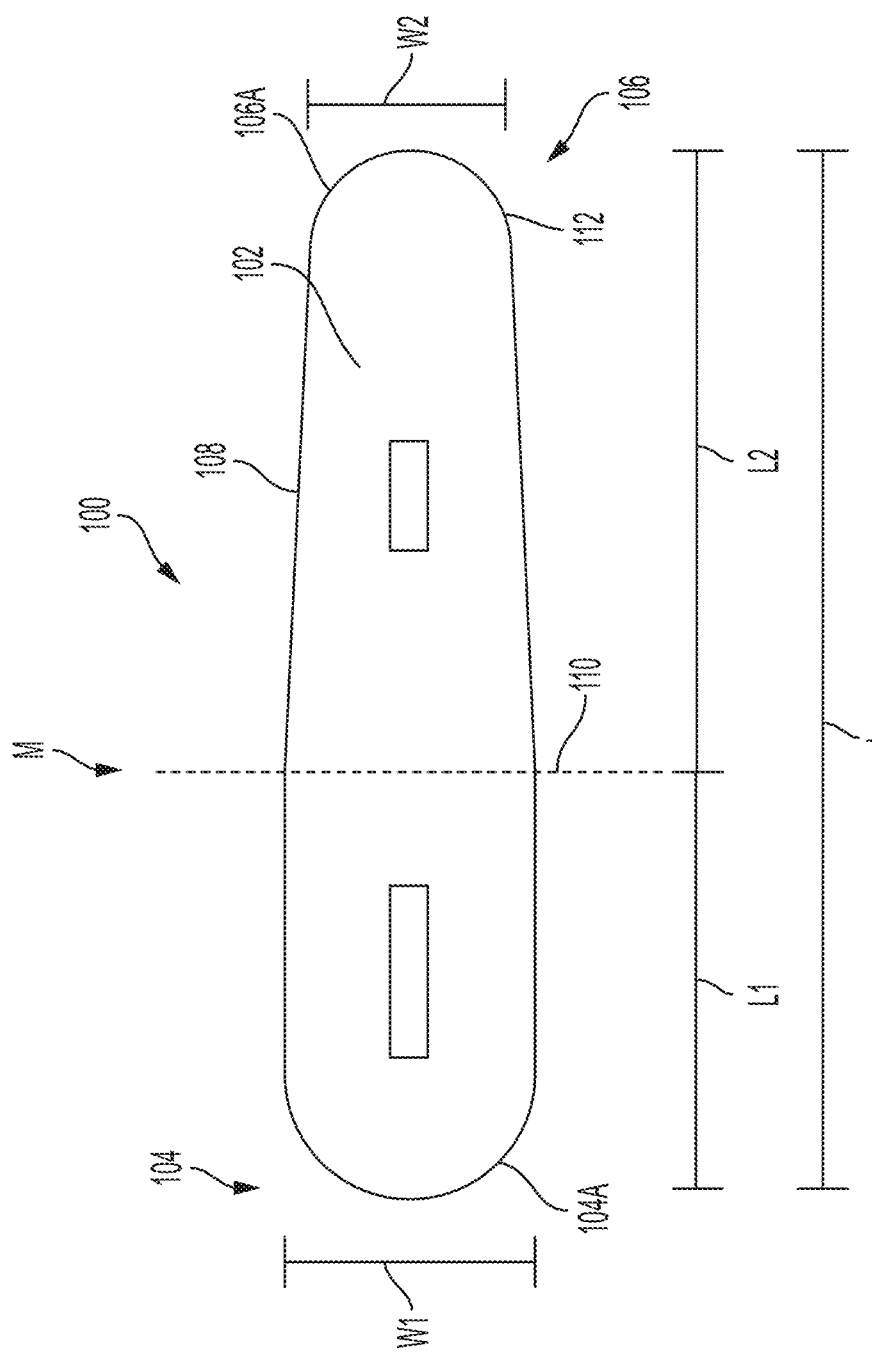

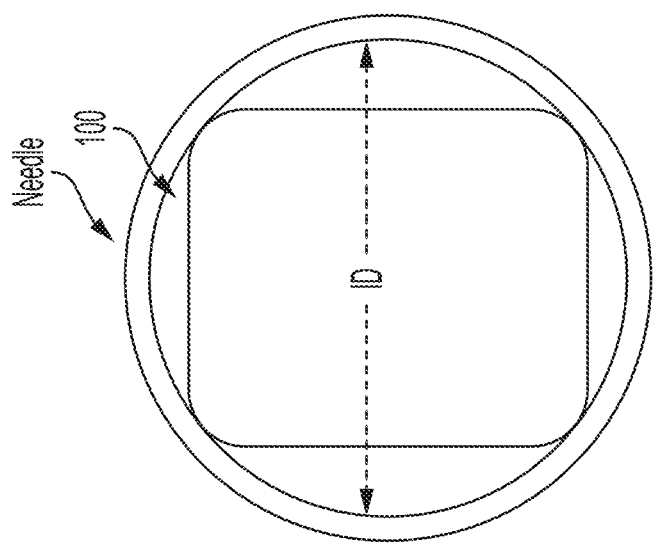
FIG. 1C
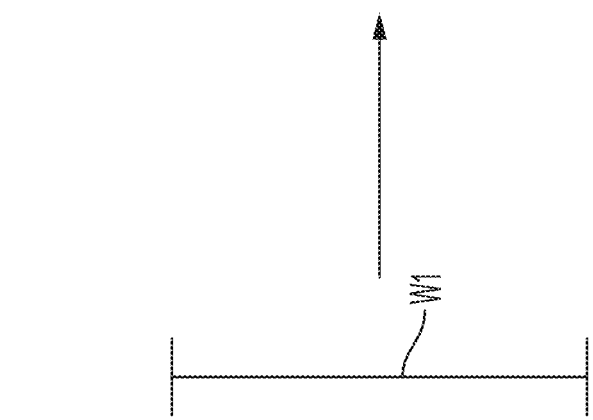
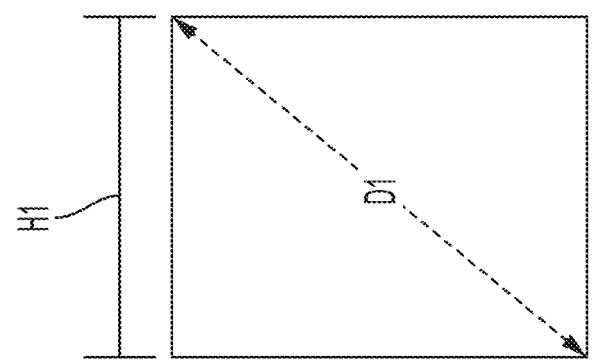
FIG. 1B

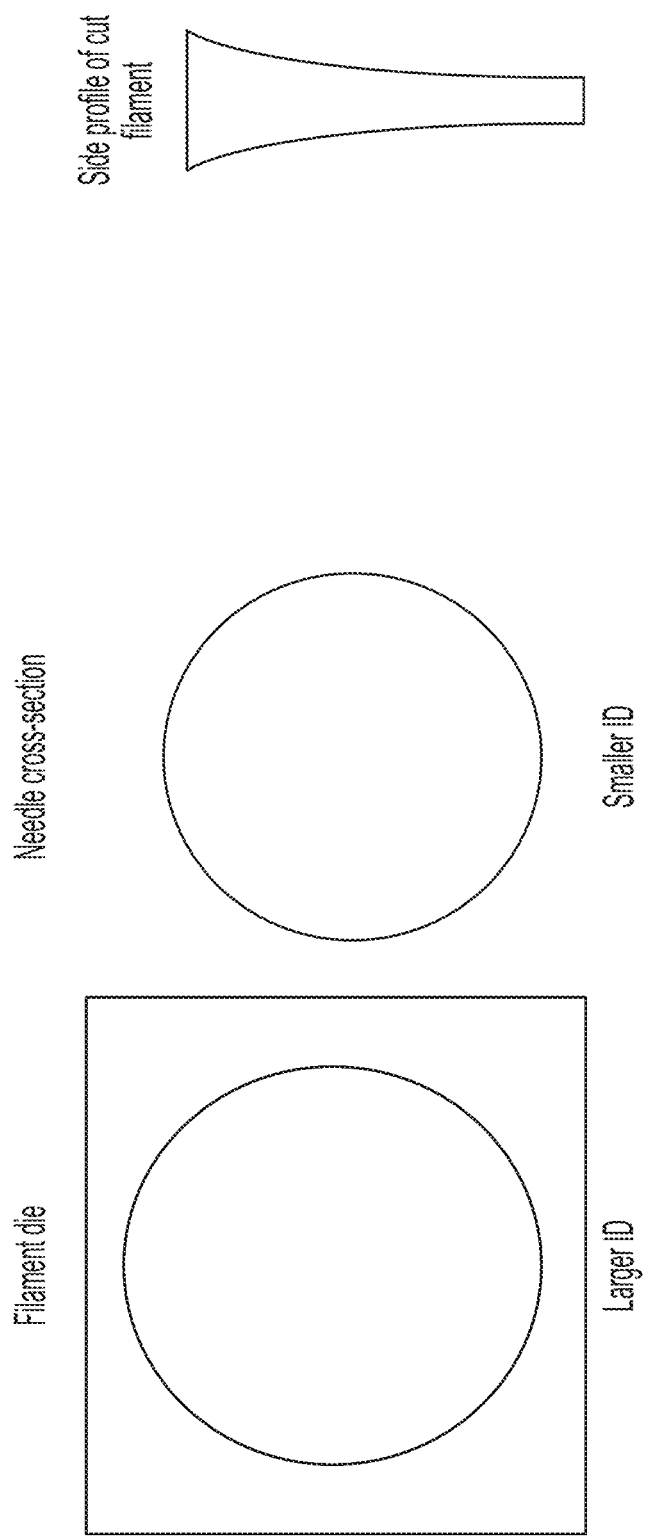

MEDICAL IMPLANT

CROSS-REFERENCE TO RELATED APPLICATIONS

The present application is a continuation of U.S. patent application Ser. No. 17/518,281, filed Nov. 3, 2021, which claims priority to U.S. Provisional Application No. 63/109,615 filed Nov. 4, 2020, and to U.S. Provisional Application No. 63/241,395 filed Sep. 7, 2021. The contents of each of these applications are incorporated by reference herein in their entirety.

BACKGROUND

A. Field

This disclosure relates generally to medical implants and methods of manufacturing those implants. More particularly, this disclosure is directed to geometrical configurations and methods of retaining a medical implant within a needle of an implant delivery device.

B. Description of Related Art

When a solution is delivered, injected or otherwise administered directly into the eye, the drug quickly washes out or is depleted from within the eye into the general circulation. From the therapeutic standpoint, this may be as useless as giving no drug at all. Consequently, solid pharmaceutically active implants that provide sustained release of an active ingredient have been developed that provide delivery within the eye of a relatively uniform concentration of active ingredients. Implants are particularly useful for providing a high local concentration at a particular target site for extended periods of time. These sustained release implants reduce the number of doses of the drug to be administered, and avoid the peaks and troughs of drug concentration found with traditional drug therapies. Use of a biodegradable drug delivery system that degrades over time has the further benefit that the spent implant need not be removed from the target site.

An intraocular implant is a drug delivery system configured to deliver medicinal products to the ocular tissue once injected into the eye. Intraocular implants are typically inserted using 22 through 27 gauge needles of an implant delivery device. The implants are typically retained within the delivery devices using a retention feature incorporated into the design of the delivery device as opposed to the implant itself. Such systems can result in retention failure where the implant falls out of the delivery device prior to completion of the implant procedure.

Prior art implant retention designs and delivery device features also can often malfunction such that the delivery of undesired particles from the delivery device into the intended site of delivery occurs.

Thus, it would be desirable to provide an implant with improved retention within the needle of the delivery device that reduces the risk of delivery device-based retention feature failure to ensure that the implant is secure until deployment and reduces the risk of introducing undesired particulate matter into the patient.

SUMMARY

The following embodiments and aspects thereof are described and illustrated in conjunction with systems, tools and methods which are meant to be exemplary and illustrative, not limiting in scope.

In one aspect, a medical implant is described. The medical implant includes a body including a first end having a first cross-sectional dimension, a second end having a second cross-sectional dimension, and a tapered portion extending between the first end and the second end. The first cross-sectional dimension is larger than the second cross-sectional dimension.

In another aspect, the tapered portion extends only partially between the first end and the second end.

In another aspect, a length of the first end of the body to a first end of the tapered portion is in a range of about 5% to about 50% of the total length of the implant.

In another aspect, a length of the first end of the tapered portion to the second end of the body is in a range of about 950 µm to about 4750 µm.

In another aspect, the body of the medical implant comprises a single layer.

In another aspect, the body of the medical implant is made of a mixture of a therapeutic or diagnostic agent and biocompatible polymers. The number and type of biocompatible polymers used, as well as their relative concentration can vary depending upon the properties of the therapeutic or diagnostic agent(s) contained in the medical implant, the location and environment in which the implant is to be inserted, and desired duration the therapeutic or diagnostic agent(s) is to elute from implant. Optionally, combinations of 1, 2, 3 or more biocompatible polymers can be used in an implant described herein. Particular examples of biocompatible polymers having applications herein are discussed infra. The duration the therapeutic or diagnostic agent is to elute from the implant can be 1 month, 2 months, 3 months, 4 months, 5 months, 6 months, 7 months, 8 months, 9 months, 10 months, 11 months, or a year or more. Optionally, the biocompatible polymer(s) of an implant described herein can include terminal esters or acids.

In another aspect, the body of the medical implant comprises a plurality of layers.

In another aspect, at least one of the plurality of layers is made of biocompatible polymers, and at least one other of the plurality of layers is made of a mixture of a therapeutic or diagnostic agent and biocompatible polymers.

In another aspect, the medical implant is formed or manufactured using a particle replication in non-wetting templates (PRINT) method to shape the medical implant.

In yet another aspect, the medical implant includes a body including a first layer, a second layer, and a third layer. The body includes a first end having a first cross-sectional dimension and a second end having a second cross-sectional dimension. The first cross-sectional dimension is larger than the second cross-sectional dimension. The body further includes a tapered portion extending between the first end and the second end. Additionally, the first layer and the third layer comprise a first material, and the second layer comprises a second material.

In addition to the exemplary aspects and embodiments described above, further aspects and embodiments will become apparent by reference to the drawings and by study of the following detailed description.

BRIEF DESCRIPTION OF THE DRAWINGS

Exemplary embodiments are illustrated in the drawings. It is intended that the embodiments and figures disclosed herein are to be considered illustrative rather than restrictive.

FIG. 1A is a top view of the medical implant of the present application;

FIG. 1B is a cross sectional view of the medical implant prior to insertion into a medical delivery device;

FIG. 1C is a cross sectional view of the medical implant inserted into the lumen of the medical delivery device needle;

FIG. 13 illustrates one possible filament die configuration that could be used to fabricate an implant of the present disclosure compared to a cannula cross-section;

FIG. 14 illustrates a cross-sectional view of an implant made using a filament die;

DETAILED DESCRIPTION

Figure 2B:
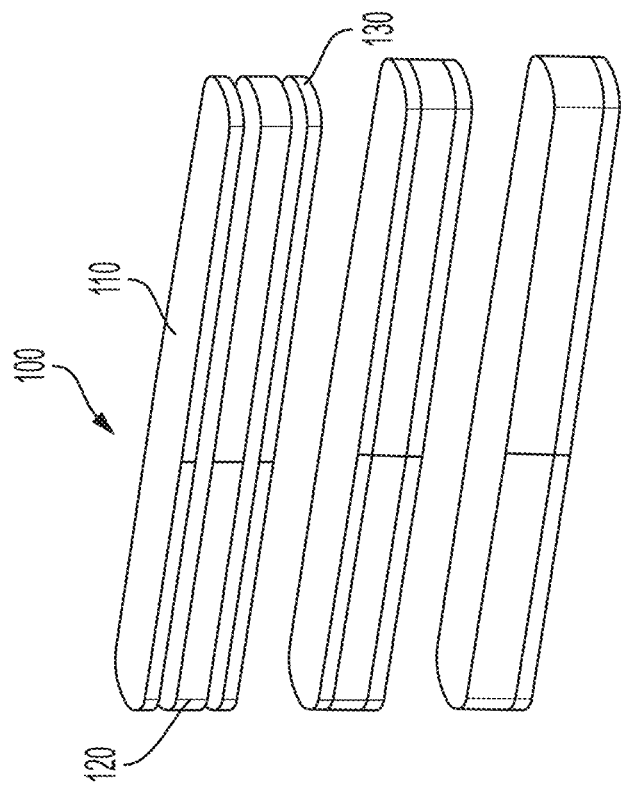
FIG. 2B is a perspective view of another embodiment of the medical implant shown in FIG. 1A.

A medical implant for use with a needle-based implant delivery device is disclosed. The medical implant is characterized by a geometrical shape that includes an outer geometry designed to create an interference fit between the inner diameter of the needle or cannula positioned adjacent to a needle and the outer surface area of the implant so that the implant is retained within the needle from the time of manufacture up until the implant is inserted and dosed to a patient's tissue. Retention within the needle is maintained during packaging, shipping, and storage of the loaded implant delivery device.

FIG. 1A shows an example medical implant 100 for use with a needle-based delivery device to deliver the medical implant into a patient's body. In one possible embodiment, the medical implant is an intraocular implant containing a drug, i.e., an active pharmaceutical ingredient (API). The medical implant 100 has an outer shape or geometry which creates a frictional force within the drug delivery device large enough to retain the implant within the drug delivery device during manufacturing, packaging, shipping, and storage of the device, but allows for the release, delivery, insertion, or implantation of the implant during administration from the delivery device into a patient's tissue upon activation of the delivery device at the time of administration.

As shown in FIG. 1A, the medical implant 100 includes a body 102 having a first end 104 and a second end 106. In one embodiment, the first end 104 has a greater or larger cross-sectional dimension W1 than the cross-sectional dimension W2 of the second end 106, so that the first end 104 is retained within the drug delivery device by frictional interference with the interior surface of the needle. As shown in FIG. 1A, the first and second ends 104, 106 may have a rounded profile 104A, 106A. In other embodiments, the profiles of the first and second ends 104, 106 may take other geometrical forms, such as rectangular prisms.

FIG. 1B shows a cross section of region L1 of the medical implant 100 prior to being loaded into the medical device with a largest diagonal length D1. D1 is related to W1 and H1 by the relationship, $D1=\sqrt{H1^2+W1^2}$.

D1 is preferably predetermined and configured to be greater than a nominal inner diameter (ID) of the needle that it will be inserted into and retained therein (see FIG. 1C). In some embodiments, D1 has a length of 104% of the nominal inner diameter (ID) of the needle that it is retained in, which may be in the range of about 105% to about 102.5% of the nominal ID of the needle. In some embodiments, D1 has a length of 102.5% of the nominal inner diameter (ID) of the needle that it is retained in, which may be in the range of about 104 to about 100.5% of the nominal ID of the needle. For 27 G needles, the ID may be in the range of about 292.1 µm to about 330.15 µm. For 25 G needles, the ID may be in the range of about 393.7 µm to about 431.8 µm. The implants of this this disclosure can be configured to be retained in needle sizes in the range of from 21 G to 30 G.

Referring again to FIG. 1A, in some embodiments, the length L of the body 102 may be in the range of about 1000 µm to about 5000 µm. In some embodiments, the body 102 includes a tapered portion 108 extending between the first end 104 and the second end 106. In some embodiments, the tapered portion 108 extends only partially between the first end 104 and the second end 106. For example, the tapered portion 108 begins at some midpoint M 110 between the first end 104 and the second end 106. In one example embodiment, a length L1 of the first end 104 of the body extends to the midpoint 110, which is also a beginning end of the tapered portion 108, and can be in a range of about 5% to about 50% of the total implant length L. Similarly, a length L2 of the second end 106 of the tapered portion 108 starting from the midpoint 110 and terminating at a second end 112 of the tapered portion 108 is in a range of about 10% to about 90% of the total implant length L. In some embodiments, the tapered portion 108 may define the entire the second end 106 of the body 102.

Figure 2A:
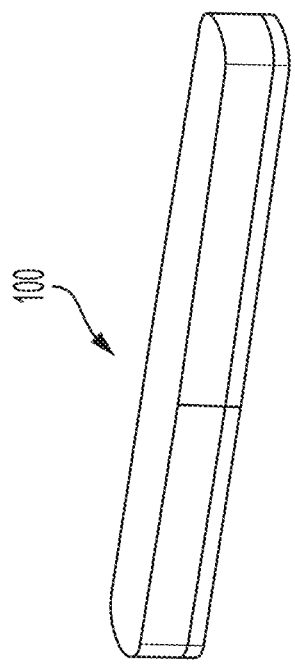
FIG. 2A is a perspective view of one embodiment of the medical implant shown in FIG. 1A.

In one embodiment, the medical implant 100 is monolithic, or comprises a single layer, as shown in FIG. 2A. In this embodiment, the medical implant 100 may be comprised of a therapeutic agent, dexamethasone, for example and poly(D, L-lactic-co-glycolic acids)(PLGAs), for example. In other embodiments, the medical implant may be comprised of a mixture of a therapeutic agent, monotosylate ((S)-4-(3-amino-1-(isoquinol in-6-yl-amino)-1-oxopropan-2-yl)benzyl alcohol monotoluenesulfonate; (S)-3-amino-2-(4-(hydroxymethyl)phenyl)-N-(isoquinolin-6-yl)propanamide monotosylate), for example and polyesteramide (PEA) polymers or any other suitable materials.

Prostaglandins, and analogs or derivatives thereof, having applications as a therapeutic agent in a pharmaceutical implant composition of the present disclosure include latanoprost, bimatoprost, travoprost, tafluprost, 3-hydroxy-2,2-bis(hydroxymethyl)propyl 7-((1r,2r,3r,5s)-2-((r)-3-(benzo[b]thiophen-2-yl)-3-hydroxypropyl)-3,5 dihydroxy-cyclopentyl)heptanoate (chemical structure (II)), cloprostenol isopropyl ester, 13,14-dihydrocloprostenol isopropyl ester, latanoprostene bunod, unoprostone, $PGF_{1\alpha}$ laisopropyl ester, $PGF_{2\alpha}$ a isopropyl ester, $PGF_{3\alpha}$ isopropyl ester, fluprostenol, or any combination thereof. In some embodiments, the prostaglandins, and analogs or derivatives thereof, having applications as a therapeutic agent include dukeprost, tiaprost, or both. In some embodiments, the prostaglandins, and analogs or derivatives thereof, having applications as a therapeutic agent include free acids, and pharmaceutically acceptable salts thereof, of the prostaglandins and analogs or derivatives thereof.

Other therapeutic agents having applications in a pharmaceutical implant composition of the present disclosure for treating an ocular disease or disorder, e.g. glaucoma, include but are not limited to beta blockers, miotics, alpha adrenergic agonists, or carbonic anhydrase inhibitors, and antimetabolites such as 5-fluorouracil or mitomycin C.

Naturally, a pharmaceutical composition of the present disclosure can comprise a therapeutic agent, or a combination of two or more therapeutic agents, examples of which are discussed above. Moreover, analogs or derivatives, pharmaceutically acceptable salts, zwitterions, solvates, esters, and polymorphs of therapeutic agents, such as those discussed herein, have applications in a pharmaceutical composition of the present invention. As used herein, an "analog" is a compound having a structure similar to that of another compound (its "parent" compound) but differing from it in respect to a certain component. The analog can differ from its parent compound in one or more atoms, functional groups, or substructures, which are replaced with other atoms, groups, or substructures. Likewise, an analog of a parent compound can also be formed from the replacement of particular atoms of the parent compound with radioactive isotopes of those particular atoms. A "derivative" is a compound that can be imagined to arise or actually be synthesized from a parent compound by replacement of one atom with another atom or group of atoms.

In a pharmaceutical composition of the present disclosure, a therapeutic agent is blended with a biodegradable polymer matrix to form a pharmaceutical composition. The amount of a therapeutic agent used in the pharmaceutical composition depends on several factors such as: bio degradable polymer matrix selection, therapeutic agent selection, desired rate of release in a substantially linear manner, duration of desired rate of release, configuration of pharmaceutical composition, and ocular PK, to name a few.

For example, overall therapeutic agent content of a pharmaceutical composition of the present disclosure may comprise approximately about 0.1 to approximately 60.0 weight percent of the total pharmaceutical composition. In some embodiments, the therapeutic agent comprises from about 1% to about 90%, or about 1% to about 80%, or about 1% to about 70%, or about 1% to about 60%, or about 1% to about 50%, or about 1% to about 40%, or about 1% to about 30%, or about 1% to about 20%, or about 1% to about 10%, or about 10% to about 50%, or about 10% to about 40%, or about 10% to about 30%, or about 10% to about 25%, or about 10% to about 23%, or about 10% to about 20%, or about 15% to about 35%, or about 15% to about 30%, or about 15% to about 25%. All these percentages are in weight percentage. In a particular embodiment, dexamethasone comprises approximately 20.0 weight percent of the pharmaceutical composition.

A pharmaceutical composition of the present disclosure is prepared by dissolving a polymer matrix and therapeutic agent in a suitable solvent to create a homogeneous solution. For example, acetone, alcohol (e.g., methyl alcohol or ethyl alcohol), acetonitrile, tetrahydrofuran, chloroform, and ethyl acetate may be used as solvents. Other solvents known in the art are also contemplated. The solvent is then allowed to evaporate, leaving behind a homogeneous film. The solution can be aseptically filtered prior to evaporation of the solvent.

Additional implant formulation examples can be found in U.S. Pat. No. 10,624,904, which is fully incorporated by reference herein in its entirety.

In another embodiment, the medical implant 100 may be comprised of a plurality of layers. In one example, as shown in FIG. 2B, the medical implant 100 includes a first layer 110, a second layer 120, and a third layer 130. The second layer 120 is disposed between the first layer 110 and the third layer 130. In some embodiments, the first layer 110 and the third layer 130 are made of the same material. In some embodiments, the first layer 110 and the third layer 130 are comprised of a mixture of PLGAs, and the second layer 120 may be comprised of a mixture of Dexamethasone or other therapeutic drugs and PLGAs, for example. In other embodiments, the first layer 110, the second layer 120, and the third layer 130 may be comprised of any other suitable materials.

Although the medical implant 100 is shown as having three layers, it should be understood that in other embodiments, the implant may comprise any number of layers.

Figure 3A:
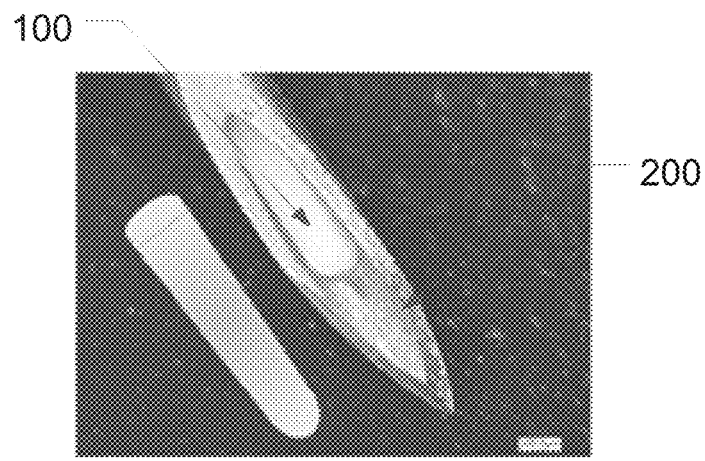
FIG. 3A shows a view of the medical implant of FIG. 1A positioned within a drug delivery device.
Figure 3B:
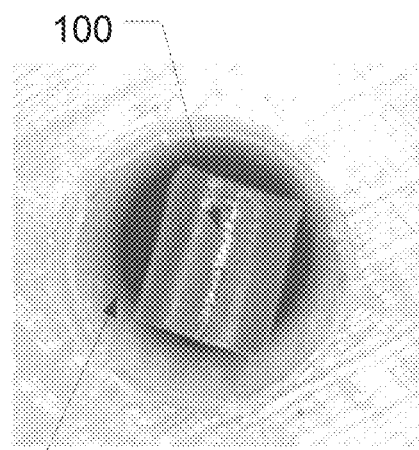
FIG. 3B shows a top cross-sectional view of the device shown in FIG. 3A.
Figure 3C:
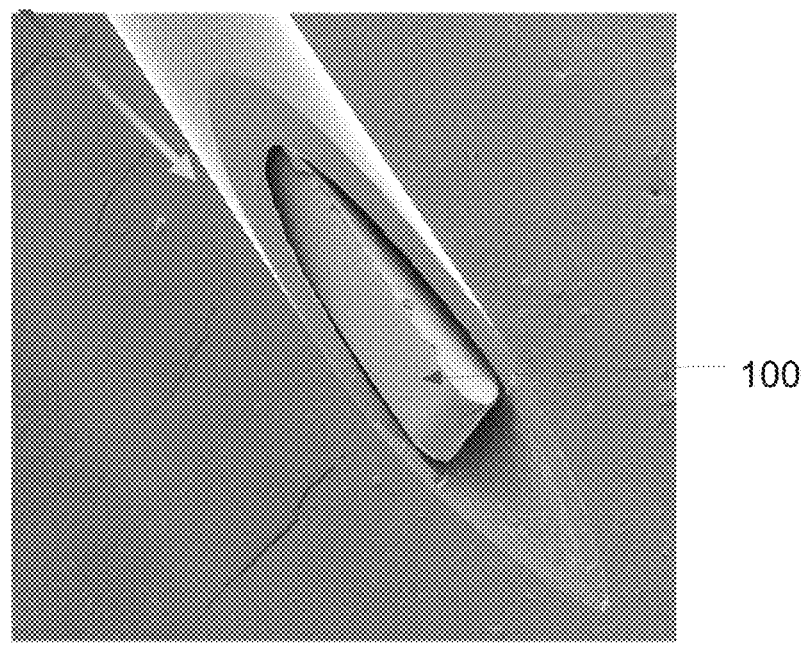
FIG. 3C shows another view of the medical implant of FIG. 1A positioned within a drug delivery device.
Figure 4:
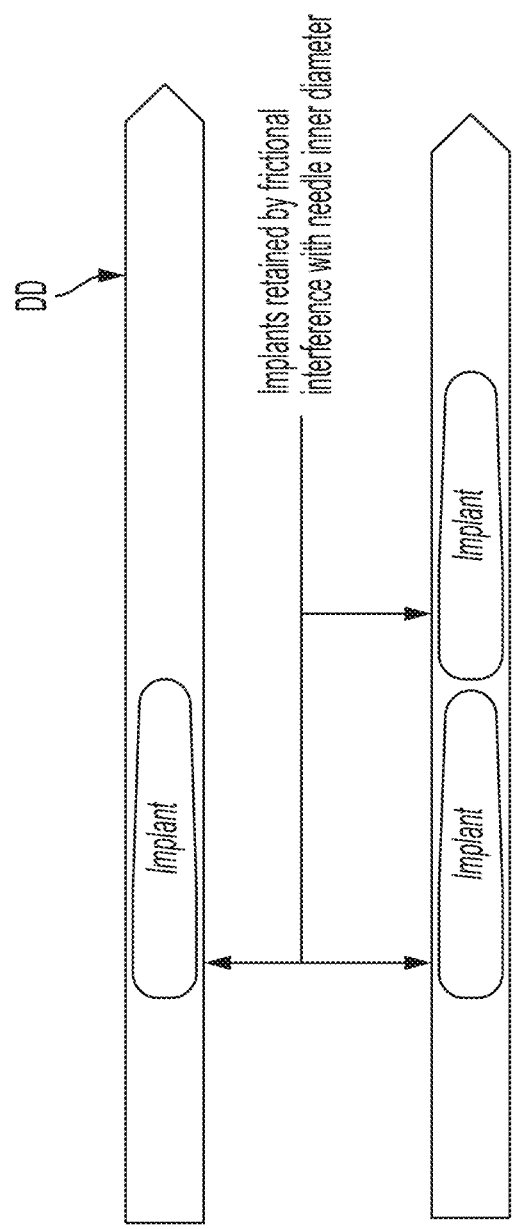
FIG. 4 shows a single and multiple medical implants positioned within the needle of a drug delivery device.

FIGS. 3A, 3B, and 3C show the medical implant 100 positioned within a needle of a needle-based drug delivery device 200, where the needle can range in size from 21 G to 30 G. As shown in FIGS. 1B, 3B, and 4 the geometrical shape, i.e., its outer geometry, of the medical implant 100 creates an interference fit with the inner diameter 202 of the needle 200 to retain the implant 100 within the needle.

In another embodiment, multiple medical implants 100 can be inserted into a single delivery device DD, as shown in FIG. 4, in order to increase the amount of medicinal product delivered, to deliver one or more medicinal products, or to deliver implants designed and configured to have one or more drug delivery profile.

Figure 5:
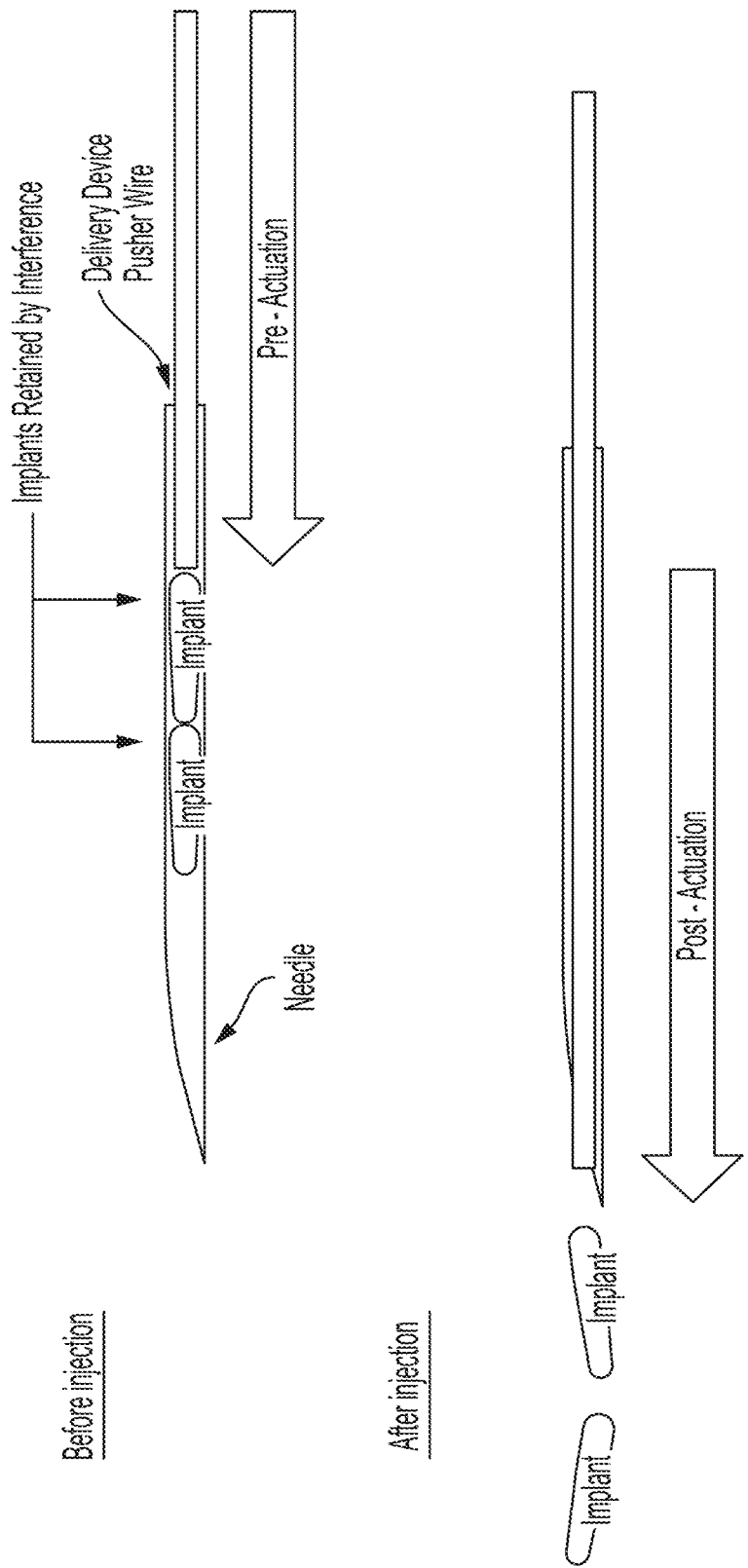
FIG. 5 shows how implants are retained in a needle based delivery device and how they are delivered using a wire pusher wire that when actuated exceeds the frictional forces between the implants and the needle lumen to deliver the implants.

FIG. 5 show examples of how implants are retained in a needle-based delivery device, and how they are delivered using a pusher wire that when actuated exceeds the frictional forces between the implants and the needle lumen to deliver the implants. The pusher wire may be propelled or actuated using a spring based, electro-mechanical based or pneumatic based device feature.

Figure 19:
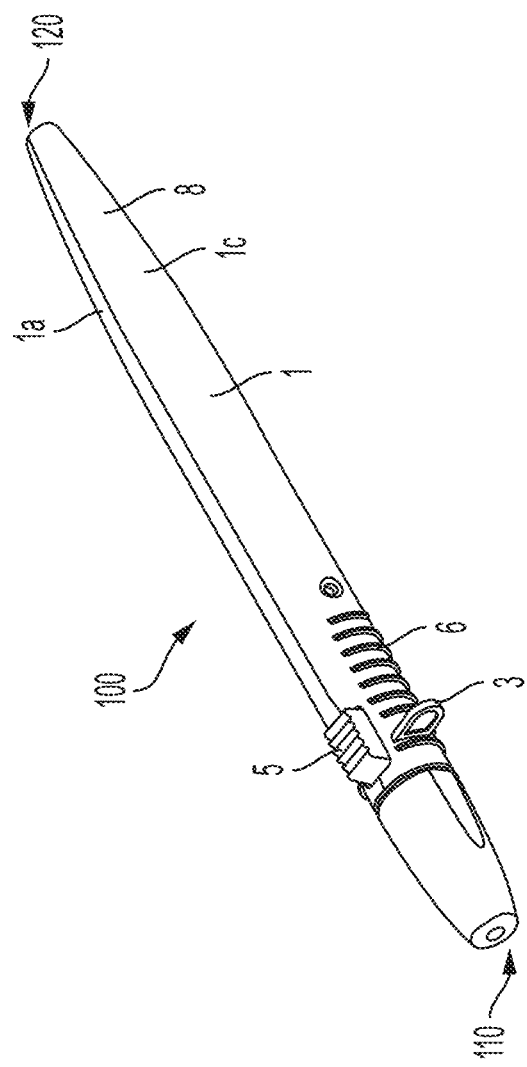
FIG. 19 is a perspective view of one possible design of a delivery device that could be used to insert an implant of the present disclosure into a patient's tissue.
Figure 20:
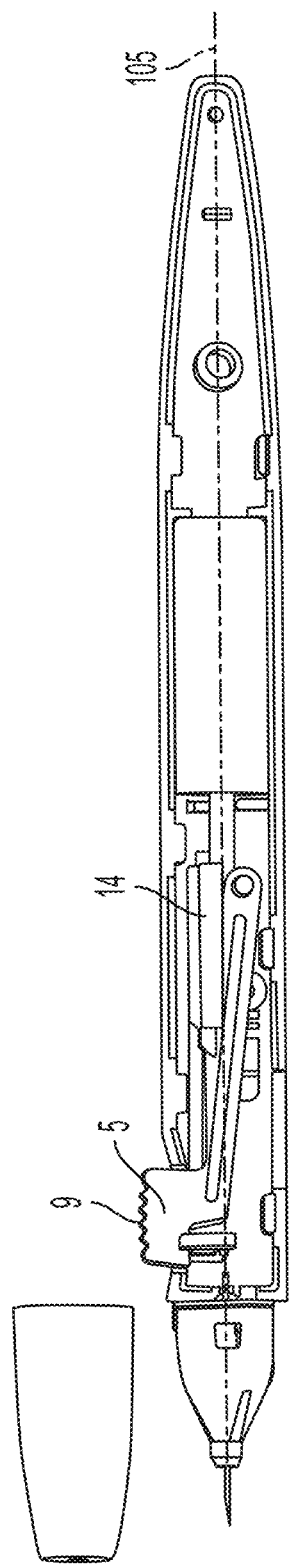
FIG. 20 illustrates a cross-sectional of the delivery device of FIG. 19.

A number of possible devices can be configured and used to deliver the implants of the present application. For example, FIGS. 19 and 20 show one possible embodiment of a delivery device 100 having an elongated substantially cylindrical body or housing 1 defining a longitudinal flow path or axis 105, the delivery device has a distal end 110 and a proximal end 120. The housing 1 can be formed from sections, for example two halves 1a and 1c, that are permanently connected to each other during assembly of the device. When assembled, the housing 1 can have a generally tapered proximal end 8 that provides an ergonomic benefit when holding and using the device to deliver the implant into tissue. The tapered proximal end can also provide a convenient prompt to the user of where on the housing to grasp/hold the delivery device. To further indicate where the user should grasp or hold the delivery device during use, the outer surface of the distal end of housing 1 can have a grip surface 6. This grip surface can be comprised of a plurality of surfaces in the form of raised or proud surfaces or ribs, knurled or roughened surfaces, inlays or overlays of a tactile/soft touch material, stippling features, dimples, or any other features that indicates to the user where to grab or hold the device during use. Another feature of grip surface 6 is that it can provide a pushing or bearing surface that the user can use to deploy the device axially in the distal direction during insertion of the needle at the desired implant insertion location site. Another device feature that can assist a user in moving or pushing the needle into the target tissue location is the raised surface of the activation member 5. In some cases, it is desirable to include a pushing surface 9 that provides the user a tactile feel and/or leverage feature during operation of the implant delivery device 100.

The housing 1 can also have a cut-out located at the distal end portion that will slidably accept lock 3 having an anvil stop surface and a retaining detent that can be configured to engage a portion of the housing 1 to prevent premature or unintended disengagement from a locked position. Lock 3 is configured to have two positions, a locked position and an unlocked position. FIGS. 19 and 20 show the lock 3 in the first or locked position where the anvil stop surface abuts and prevents movement of the activation member 5, which in turn prevents activation of the implant delivery device. The second or unlocked position is where the user has removed and physically separated lock 3 from the housing 1, for example by pulling the lock transversely relative to the longitudinal axis 105 to overcome the reversible retaining detent. Once lock 3 is removed from the delivery device 100, the activation member 5 is no longer blocked from moving relative to both the housing and the shuttle assembly 14, more specifically shuttle 18. When in the first or locked position, lock 3 can function as anti-rolling feature. i.e., the protruding structure of the lock will prevent the delivery device from uncontrollably rolling on a flat surface, such as, inadvertently rolling off a tabletop. A gripping tab can be provided that extends radially from the lock past the outside surface of the housing and is shaped so that a user can grasp lock 3 to remove it from housing 1.

Other examples of delivery devices include, but are not limited to, the devices shown and described in U.S. Pat. Pub. No. 2019/0374380, U.S. Pat. No. D592,746, U.S. Pat. Nos. 9,039,761, and 10,258,503.

One possible method of manufacturing or forming the medical implant 100 is a particle replication in non-wetting templates (PRINT) method and technology to obtain the shaped medical implants 100 of this disclosure. The geometric shape of the medical implant 100 can be easily changed during the manufacturing process by changing the geometry of the mold tooling features used to form the implants using PRINT technology.

Figure 6:
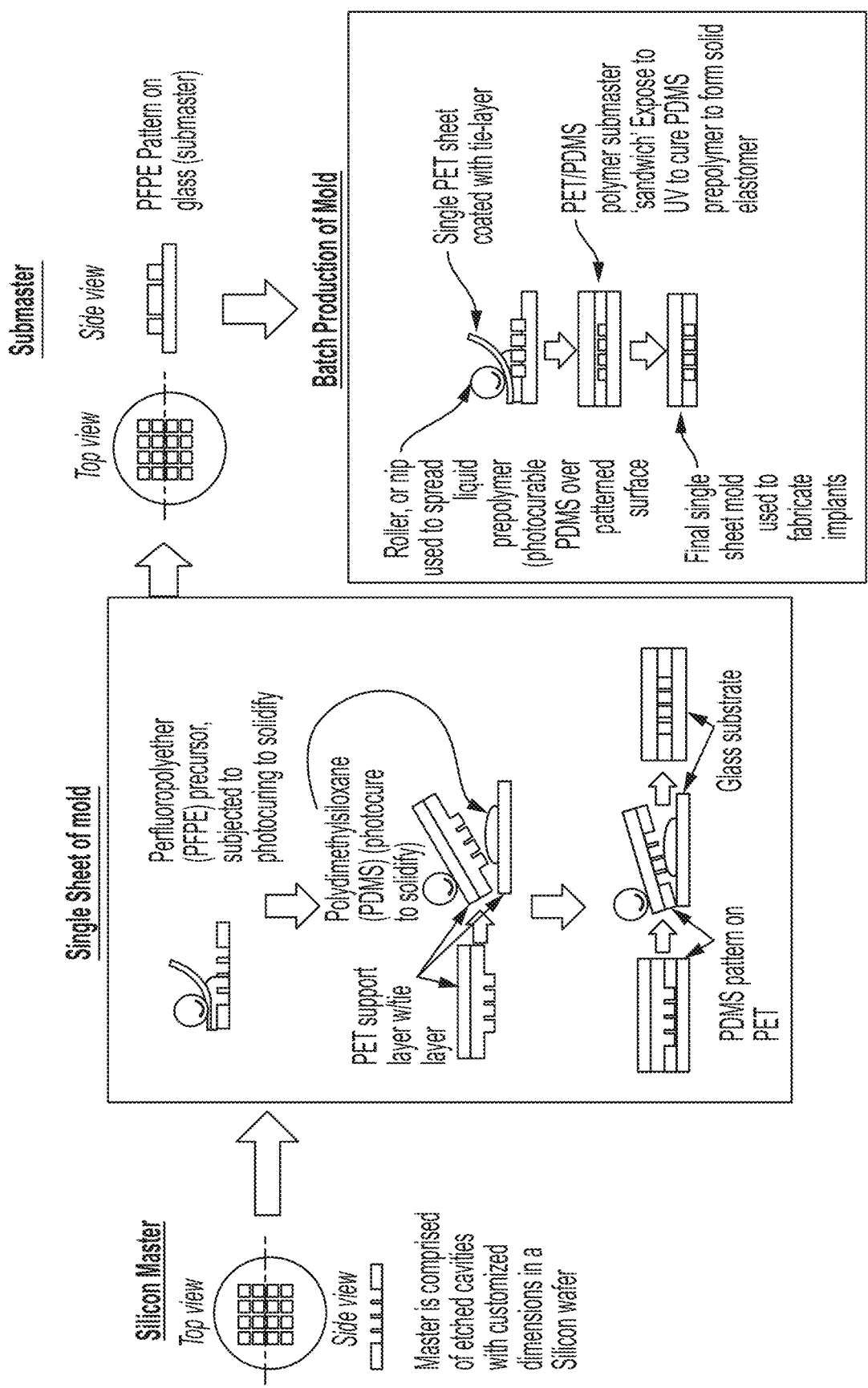
FIG. 6 is an illustration summarizing one possible method used to fabricate PRINT (Particle Replication in Non-wetting Templates) molds containing customizable feature geometries and dimensions for the fabrication of implants.

FIG. 6 illustrates the top view of a PRINT mold feature whose geometry can be modified to produce implants with different geometrical shapes, as further described in U.S. Pat. No. 10,624,904, the teachings of which are incorporated fully herein by reference.

Figure 7:
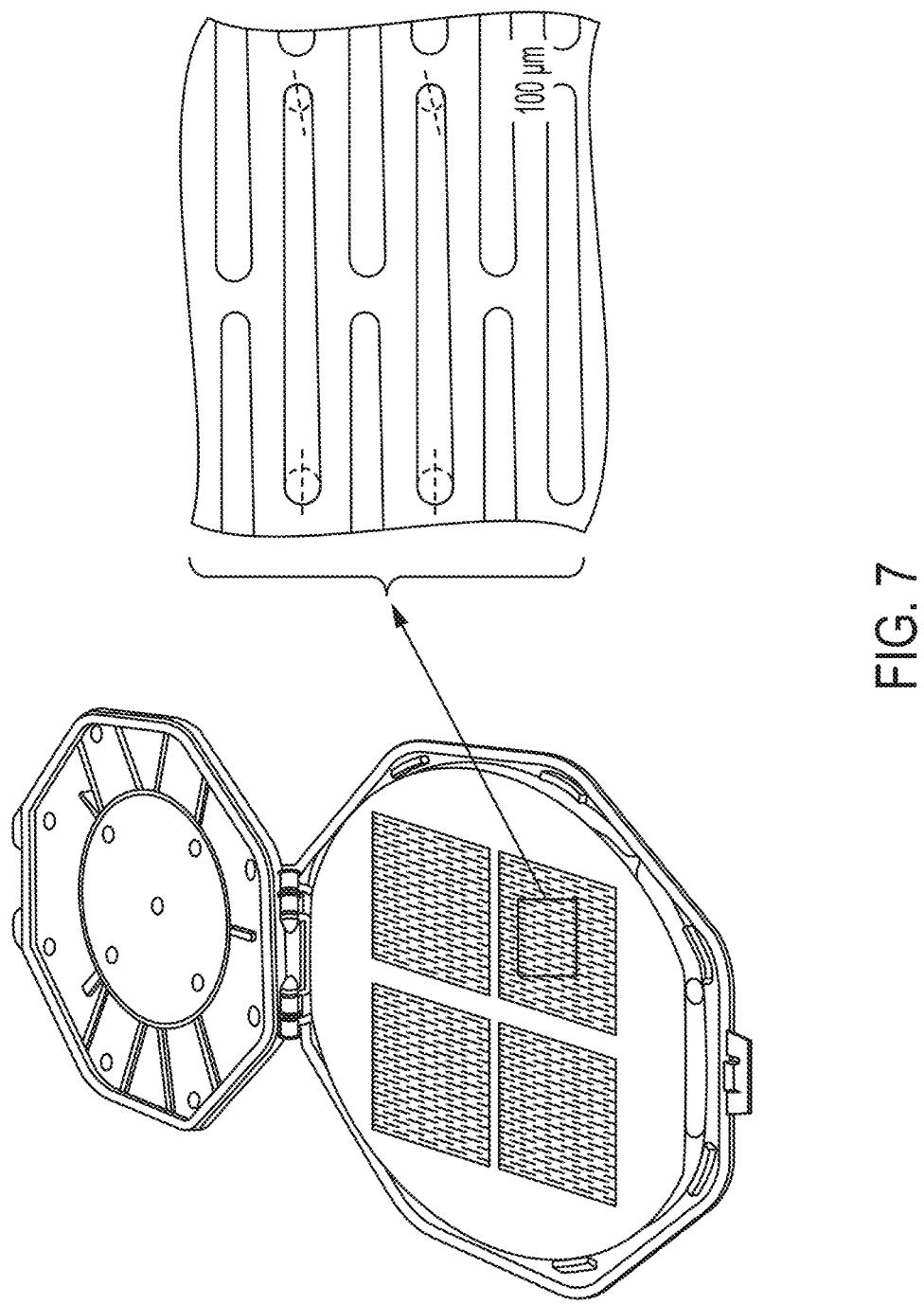
FIG. 7 is a microphotograph showing the top view of a laser etched Silicon Master showing the geometrical features used to fabricate molds for the production of PRINT implants.
Figure 8:
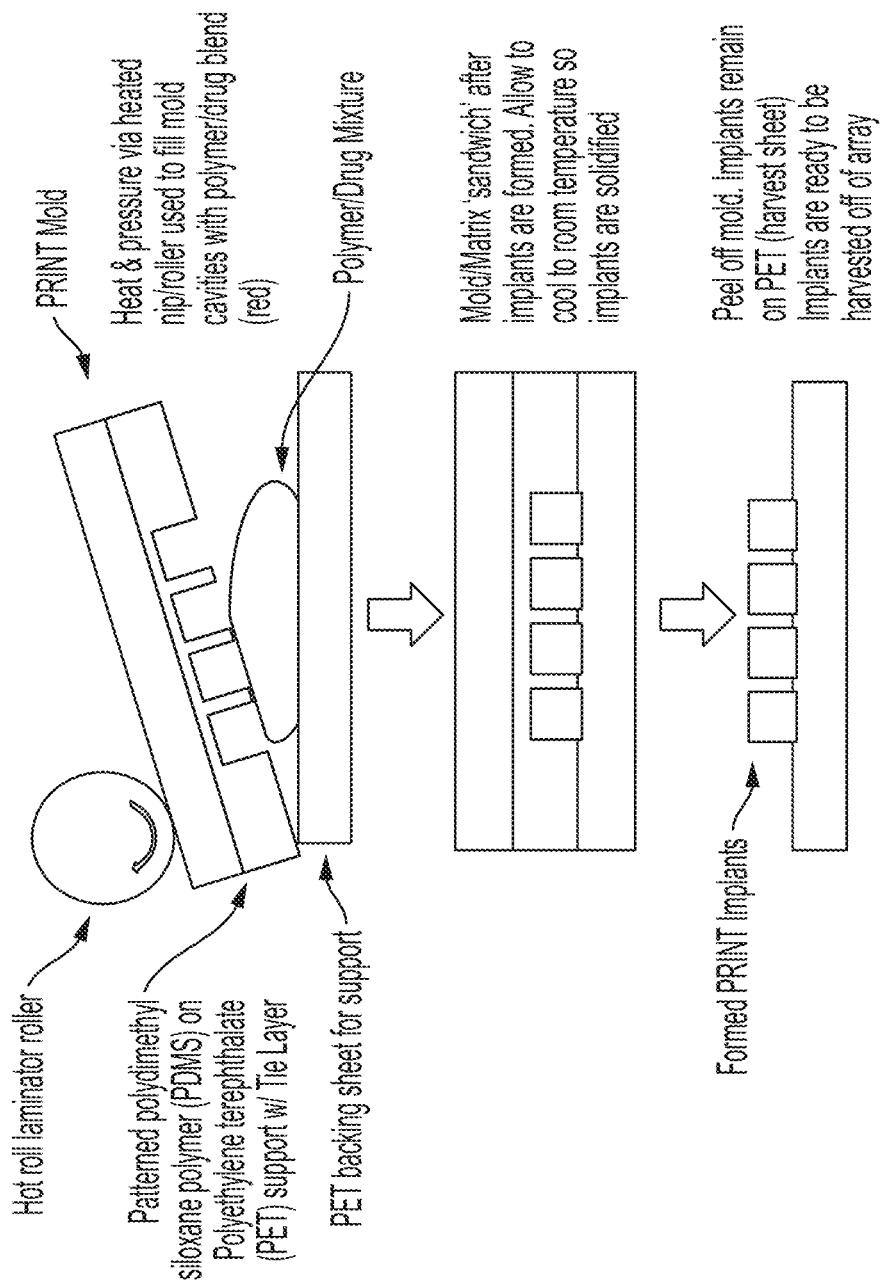
FIG. 8 is an illustration summarizing the PRINT molding process used to fabricate implants with customizable geometrical shapes and dimensions.

FIG. 7 and FIG. 8 show the stepwise process used to make implants with customizable geometries for the fabrication of micron sized medical implants. In the PRINT manufacturing process, a flexible elastomer mold is designed to have a cavity matching the 2-D planar projection of the implant. A rigid material is etched or machined to produce an array of features of a consistent depth with a repeating planar X and Y axis design having one end of the prism of a larger diagonal than the ID of the delivery needle and one end of the prism tapered to a smaller diagonal than the ID of the delivery needle. The rigid mold is replicated to create a flexible template consisting of inverted features that can be described as posts. The flexible template is replicated to create the flexible mold or tooling consisting of cavities. The flexible template and flexible mold are designed so that it is easy for materials to release from their surfaces. To produce the implants using the PRINT manufacturing technique, the matrix material is heated, and pressure is applied to a laminate of the flexible mold, the matrix material film, and a flexible substrate. The matrix material fills the flexible mold cavities as the laminate is heated and compressed. The flexible mold is released from the matrix material to present an array of the tapered prism features adhered to a flexible substrate.

Further details of the PRINT method and technology are described in detail in U.S. Pat. Nos. 7,976,759, 8,439,666, 8,662,878, 8,944,804, 8,945,441, 9,314,548, 9,340,001, 9,545,737, and 9,662,809, all of which are incorporated by reference herein in their entireties.

Further methods to fabricate the tapered prism or trapezoidal prism or wedge style prism shaped implant of the present disclosure include die-formed extrusion, filament extrusion, injection molding, compression molding and stamp molding. These methods can produce an implant having a portion of the prism length with a larger diagonal dimension than the inner diameter (ID) of the delivery needle and a portion of the prism length with a smaller diagonal than the ID of the delivery needle. The design of a two-dimensional (2-D) form can serve as one possible starting point for different manufacturing techniques. A 2-D form defines the perimeter of the target shape, and another processing step can then be used to control the undefined third dimension which can be referred to as the z-dimension or z-axis. Still other manufacturing techniques can utilize a three-dimensional design e.g., 3-D Printing, Layer by Layer manufacturing, or additive (lamination) manufacturing. Still more manufacturing techniques can combine a coating or additive manufacturing process and 2-D form manufacturing techniques to create an implant with a portion of the length of the shape having a diagonal or diameter larger than the ID of the delivery needle and a portion of the length of the shape that has a diagonal or diameter smaller than the ID of the delivery needle.

The initial step of creating a 2-D shape is to fabricate a die, or tool, to form the implant matrix material. This can be accomplished by machining or etching metal, ceramic, silicon, or other known tool making materials. These materials can hold their shape when processed.

Figure 12:
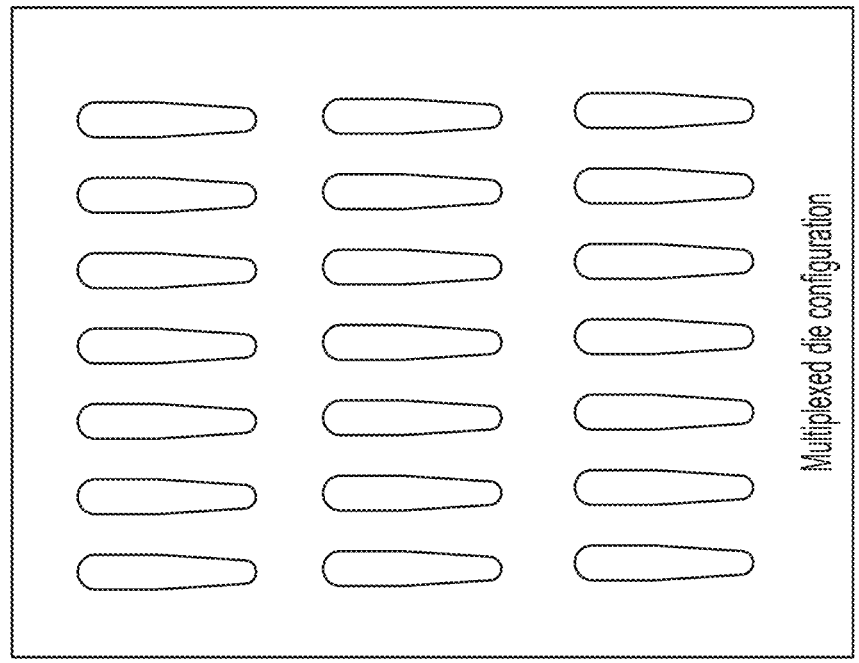
FIG. 12 illustrates a multiplexed die configuration that could be used to fabricate an implant of the present disclosure.
Figure 11:
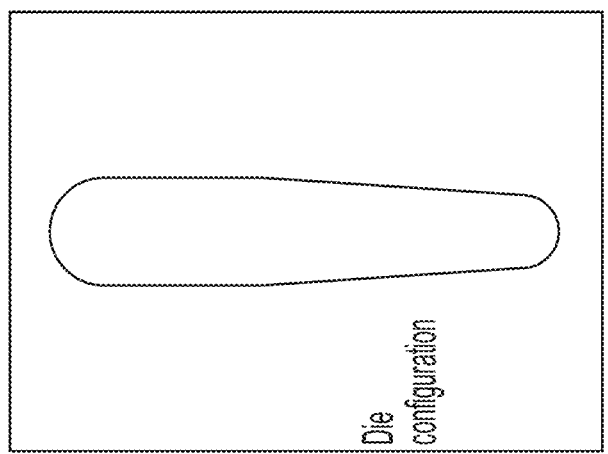
FIG. 11 illustrates a single die configuration that could be used to fabricate an implant of the present disclosure.

For die extrusion, a 2-D projection of the X and Y planar design would be etched to make the die opening shape as exemplified in FIG. 11. The matrix material would be pushed through the die shape using a combination of heat and pressure. The pressure could be pneumatically actuated or mechanically driven using intermeshed screws. To achieve appropriate control of the heat applied to the matrix material, an electrical heating element would be used. The material could be fed to a die with a single opening. A die could be constructed to have multiple openings of the same planar design to increase throughput as in FIG. 12. Each opening would be fed by the same matrix material. Alternatively, a divided matrix feed pathway could be used to coextrude multiple formulations within a single extruded geometry. The coextrusion could be used to create a wedge shaped form of one of the matrix components expanded after the die to generate a section of the 3-D shape larger than the ID of the dosing needle cannula.

For filament extrusion the matrix material could be mixed using an extruder as described above for die extrusion. A filament die of a diameter that is larger than the ID of the target needle cannula would be attached to the end of the extruder barrel. FIG. 13 depicts an example comparison between the larger filament die and the target needle cross-section view. The circular extrudate from the extruder would be drawn using variable extensional stress to achieve the tapered filament sections along the length of the extrudate. See FIG. 14 for an example of the side profile depiction of the filament extrudate. Using a cutting mechanism, the filament extrudate would be cut into sections to produce implants of a controlled length. The filament extrudate would have a diameter narrower than the target needle cannula to provide a sufficient lead-in to the target delivery needle during the loading of the implant into the needle cannula. The filament extrudate would have increasingly thicker diameter moving from the narrow or tapered end of the cut section to the interference end of the cut section.

Figure 15:
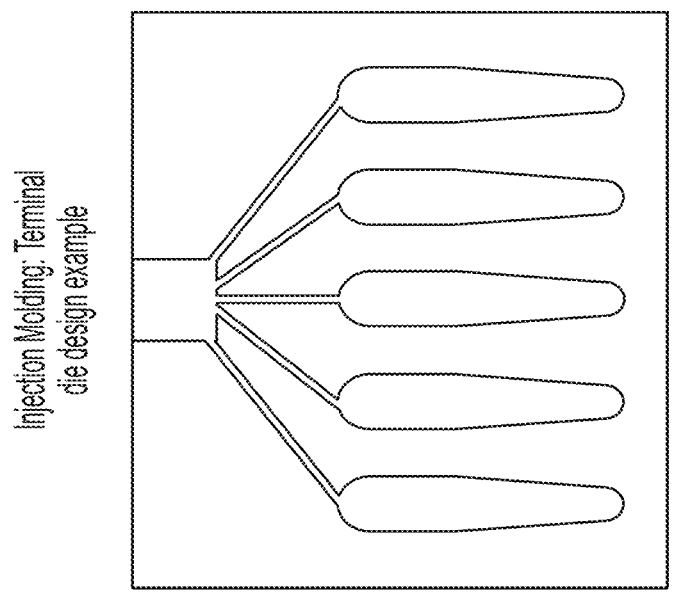
FIG. 15 illustrates one possible terminal die design that could be used in an injection molding process to fabricate an implant of the present disclosure.

For an injection molding process to form the implant of the present disclosure, the rigid mold would have a cavity feature that projected the 2-D planar view of the intended implant geometry. The mold and the individual cavities could be machined, or 3-D printed, to produce the final shape. The cavities would have a tapered profile to produce a cylindrical or prism shape having one end of the cylinder or prism smaller than the ID of the delivery needle and one end of the cylinder or prism larger than the ID of the delivery needle. FIG. 15 illustrates one possible design of an injection molding die.

Figure 16:
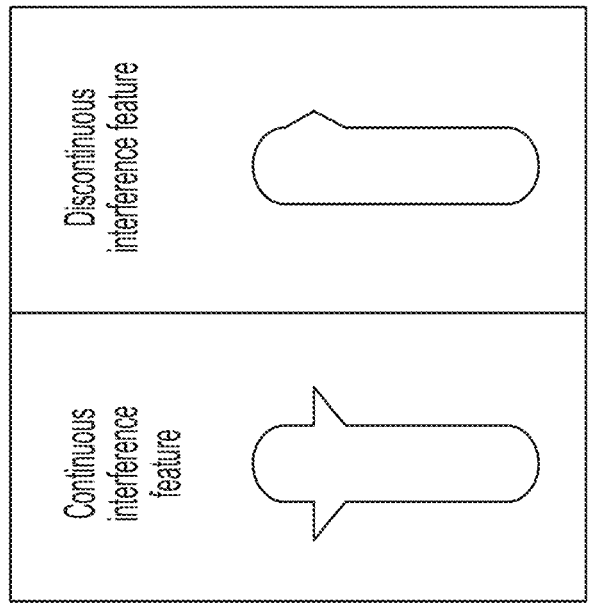
FIG. 16 illustrates cross-sectional views of implants of the present disclosure having interference features.

When injection molding is used to fabricate the implants of the present disclosure, any number of cavities per injection molding dies can be used. The sprue and runner configuration of the injection molding die would be designed to have channel diameter reduction based on proximity to the terminal cavities. The terminal connection can be placed so that the flashing from the removal of the individual part would not alter the side profile of the implant. An example of the connection placement that would not alter the side profile would be at the top tip end or bottom tip end of the implant, see FIG. 15. The design of the injection molding die also allows for the introduction of an interference feature along the side profile of the implant cavity, for example a flange design. The interference feature could be designed to provide a controlled amount of resistance for retention and controlled amount of resistance for ejection speed. The interference feature would make the implant diameter or diagonal profile larger than the ID of the delivery needle. The interference feature could be a continuous feature around the circumference or perimeter of the implant, or it could be a discontinuous feature on the circumference or perimeter of the implant, e.g., a feature on one face of a prism or one point along the circumference of a cylinder. FIG. 16 shows an example of a continuous interference feature and discontinuous interference feature.

Figure 17:
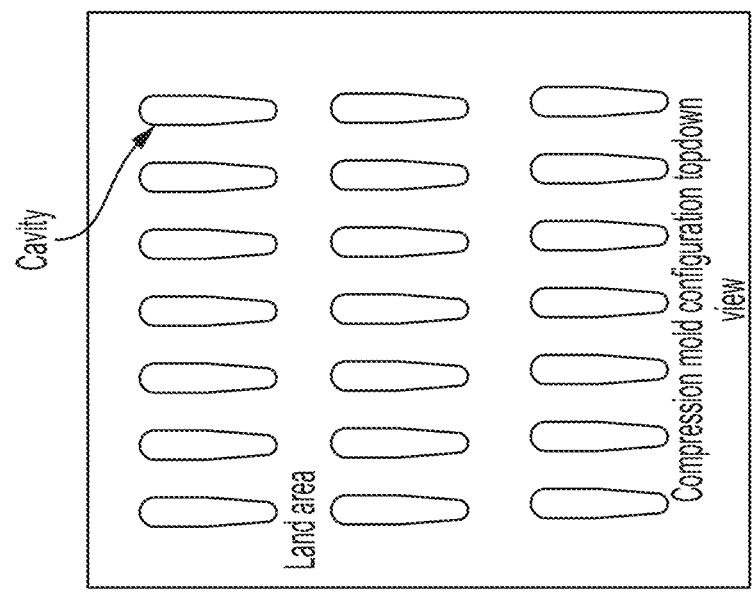
FIG. 17 illustrates one possible compression mold configuration design that could be used to fabricate an implant of the present disclosure.

For compression or stamp molding, the rigid mold or die is designed to have a cavity matching the 2-D planar projection of the desired implant. The rigid material is etched or machined to produce an array of features of a consistent depth with a repeating planar X and Y axis design having one end of the prism of a larger diagonal than the ID of the delivery needle and one end of the prism tapered to a smaller diagonal than the ID of the delivery needle (see FIG. 17). The matrix material is heated using a temperature-controlled heating element and compressed using a pressure-controlled press that can use pneumatics or hydraulics. Compression or stamp molding involves the use of 2 rigid platens that are brought together to fill the die cavities with the matrix material. The die design could be a flat surface mated with a patterned mold platen. Alternatively, the die design could involve a patterned array of cavities on both mold platens where the combined depth of the cavities on each mold face equals the target implant thickness in the z-axis. After the platens achieve complete compression, the matrix cools and is released from the mold cavities.

For 3-D printing or Layer-by-Layer manufacturing, the construction of the implant utilizes precise spatial deposition of the matrix material. The precise spatial deposition of matrix material is typically achieved through robotics, automation, and computer assisted drawings. A computer assisted drawing would be generated of an implant. The implant design would incorporate one end of the implant having a maximum diagonal or diameter larger than the ID of the delivery needle and one end of the implant having a maximum diagonal or diameter smaller than the ID of the delivery needle. The manufacturing technique for creating the implant using filament dispensing stylus would involve a dispensing tip with a diameter smaller than the smallest implant design feature. For a similar technique as in layer-by-layer manufacturing, the z-dimension resolution of the layer features must be less than the target thickness of the implant. The minimum resolution criteria enable the creation of the interference zones and non-interference zones along the implant's length.

Regardless of the method used to fabricate the implants of the present disclosure, there are post-processing modifications that are possible using the previously mentioned manufacturing modalities to create a section of the implant with one or more interference features. The initial size of the implant generated by the initial fabrication procedure would be smaller than the target cannula ID. Applying a material that has the capacity to increase in size in the presence of a specific media (e.g., hydrogels that increase in volume in the presence of water) onto the end of an implant loaded in a needle cannula. The selective addition of the second material would create the two distinct portions of the implant design where one portion of the prism length has a larger diagonal than the ID of the delivery needle. A manufacturer would fabricate the implant with a sub-needle ID diameter or diagonal using any of the techniques mentioned above. A section of the implant length would be coated with a swelling media through various techniques e.g., submersion, spray-drying, slot die coating, or vapor deposition. The swelling media can be applied as a liquid and dried or cross-linked to form a solid coating.

Figure 18:
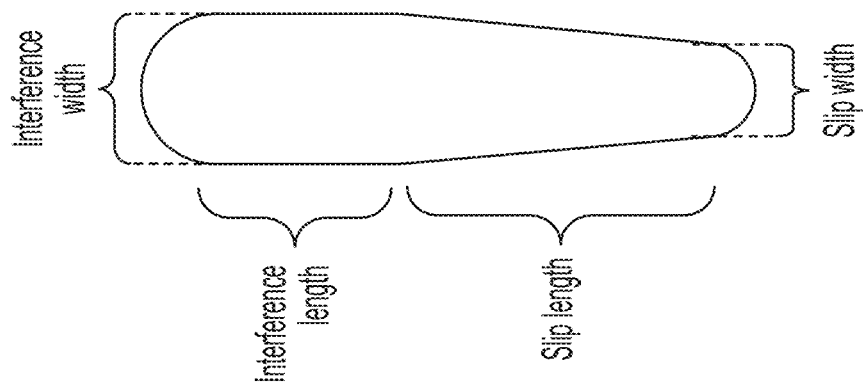
FIG. 18 illustrates a cross-sectional view of an implant of the present disclosure.

The implant shape can be described using six parameters, namely, overall length, thickness, interference width, slip width, interference length, and slip length. These six implant design parameters impact the drug product performance through three key responses. In FIG. 18, four of the parameters are shown and overall length is not shown but would be the implant length from end-to-end including both rounded end. Thickness would be captured by a projection into the z-axis. The three key responses are: (1) the resistance during loading of the implant in the delivery needle, (2) the implant's retention in the delivery needle or the resistance to movement of the implant while the implant is loaded in the delivery needle, (3) the resistance to ejection when the implant is delivered out of the needle.

The overall length and thickness parameters have a positive correlation with the three responses mentioned above. As the overall length or thickness increases, the amount of implant surface that can be in contact with the delivery needle wall or inner surface also increases. The interference width parameter correlates positively with the resistance to loading. As the interference width increases the implant diagonal increases, and the resistance during loading increases as a result. The implant's resistance to movement within the delivery needle and the implant's resistance to ejection increases with interference width until the implant's diagonal matches the ID of the delivery needle. At interference widths where the implant diagonal is above the ID of the delivery needle, there is no practical difference in the implant's retention performance or the resistance to ejection. Due to the shearing of material from the edges of the implant as the implant is loaded into the delivery needle, the implant's diagonal does not change once it is in the delivery needle. Once inside the delivery needle, the implant's resistance to movement and the implant's resistance to ejection do not change because the implant's diagonal has been reduced to match the ID of the delivery needle.

The interference length parameter correlates positively for all three responses. Greater interference length increases the resistance to loading, retention, and ejection based on the same rationale as the overall length and thickness. The slip width parameter impacts the loading resistance. The incorporation of the slip section or tapered design creates a lead-in to make implant loading easier. The slip width should not be so small that the mechanical strength is compromised during routine manufacturing processes including loading and ejection. The implant is preferably designed to withstand pushing another implant within the delivery needle or being pushed by a pusher wire for loading or ejection. However, if slip width is large or too similar to the delivery needle ID, then the resistance to loading increases and mechanical failure of the implant during loading may occur. The slip width cannot exceed the ID of the delivery needle. In other words, the slip length parameter impacts the resistance to loading of the implant and is negatively correlated. A properly predetermined slip width parameter should make the process of loading the implant into the needle cannula easier because resistance to loading decreases as the slip length increases. As the implant is loaded, the slip section of the implant centers the implant in relation to the delivery needle opening because the slope of the tapered prism forces the implant to orient and move parallel to the delivery needle cannula the further the implant travels into the delivery needle. Smaller slip lengths have the same impact on the three responses as larger interference lengths. Smaller slip lengths increase the resistance to loading, movement within the delivery needle, and ejection from the delivery needle.

Figure 9:
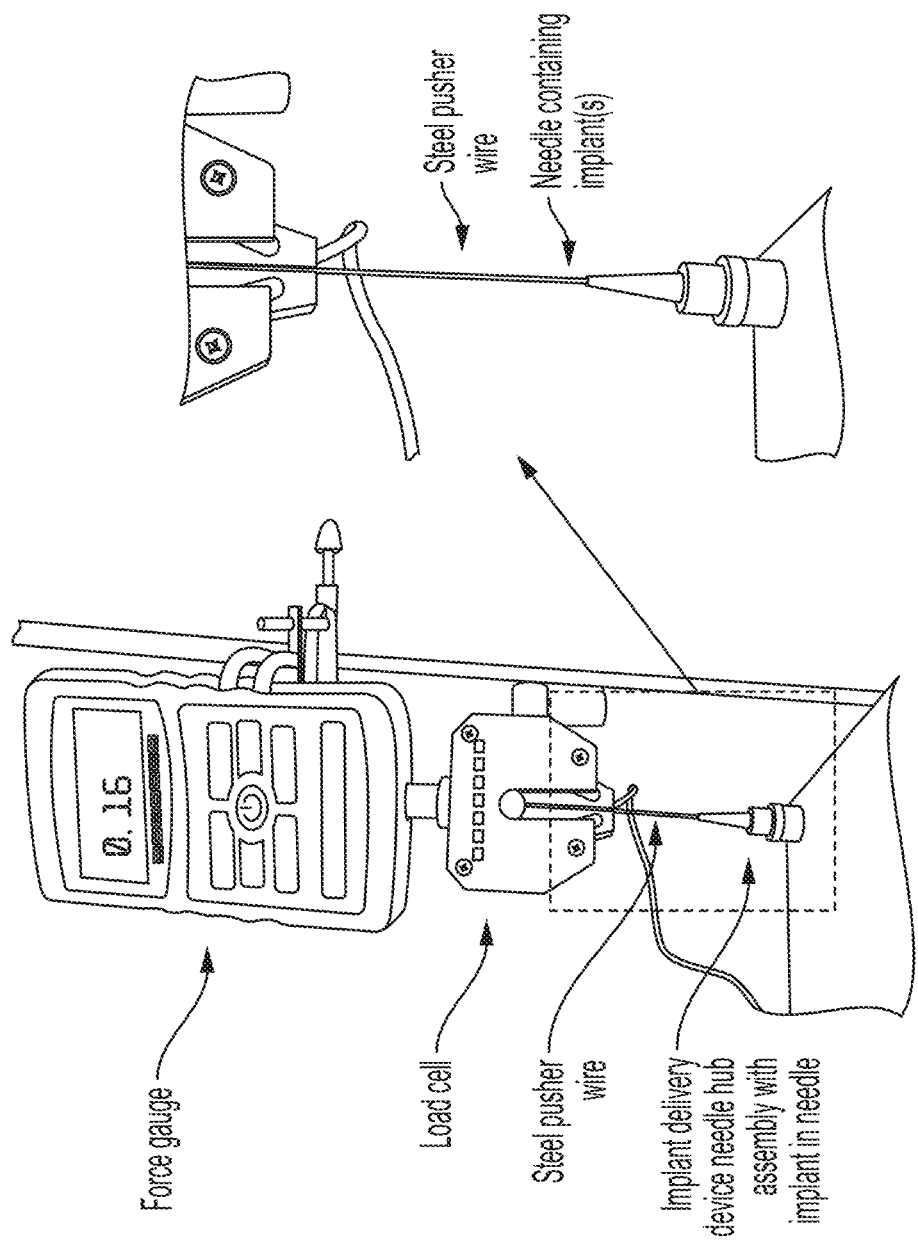
FIG. 9 shows an apparatus used to measure implant retention force.

Determination of implant retention force within a needle cannula can be obtained by measuring the force required to eject the implants from the lumen of the delivery needle, e.g., a 27 G needle. Using a narrow-gauge stainless-steel pusher rod operatively associated with a Mark-10 Model M5-10 Force Gauge, or similar force gauge, and a load cell, will provide an indication of the pusher wire force necessary to eject the implant from the inside of the needle cannula. FIG. 9 shows one example of an apparatus used to measure implant retention force. The steel pusher wire is inserted into the needle containing the implant, and advanced until the implant is disengaged from the needle. The force required to disengage the implant is measured as the retention force by the load cell.

Figure 10:
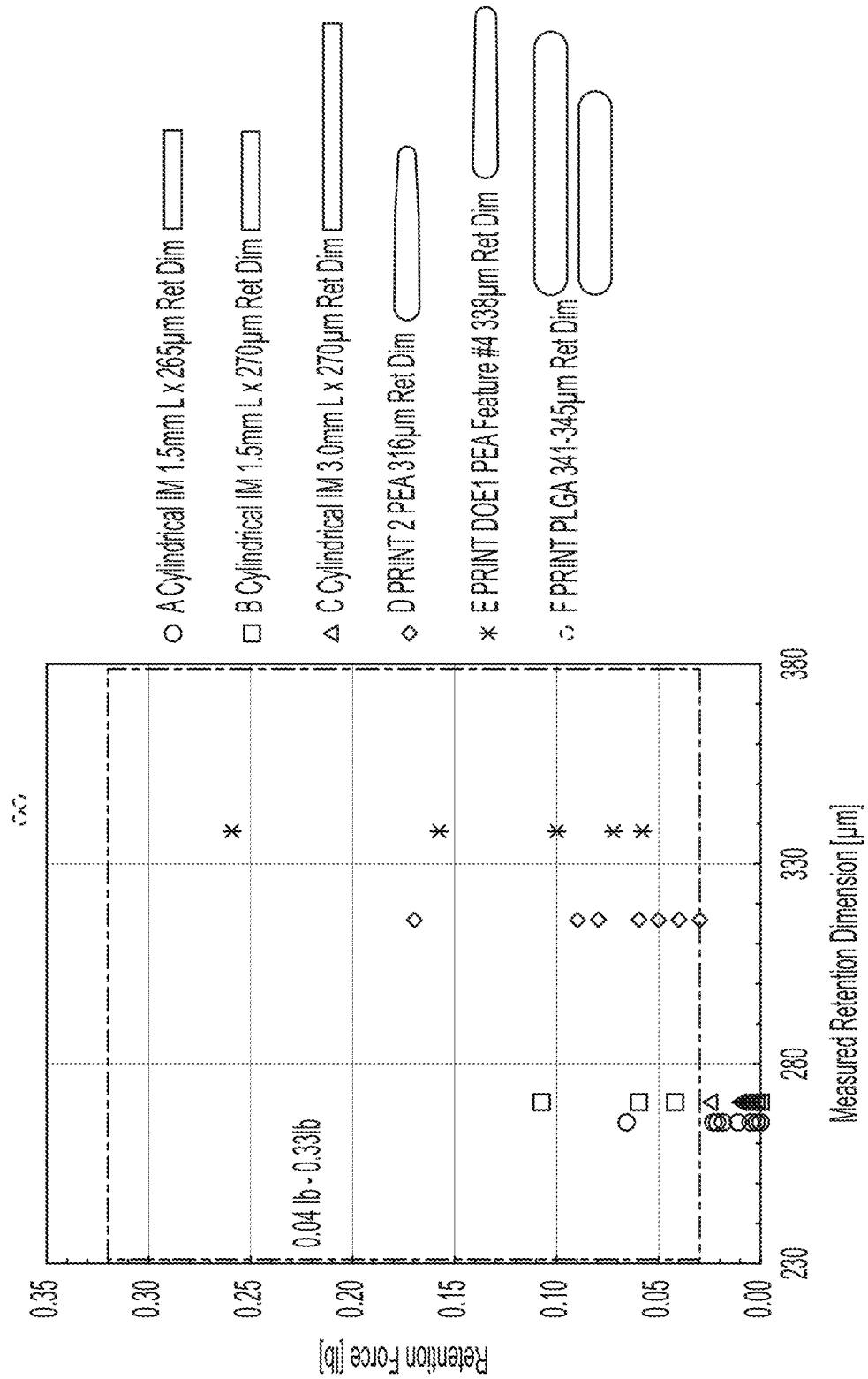
FIG. 10 is a graph showing the retention forces of a number of different shaped medical implants in a 27 G needle.

FIG. 10 is a graph showing the retention force measurements of a number of medical implants with different shapes in a 27 G needle. The numerical results and information about the implants tested are summarized in Table 1 below for implants in 27 G needles.

TABLE 1

27G Ultra-thin

Needle Gauge: wall needle
Sample Group:

| | A | B | C | D | E | F1 | F2 |
|---|---|---|---|---|---|---|---|
| Manufacturing Process: | Injection mold | Injection mold | Injection mold | PRINT | PRINT | PRINT | PRINT |
| Implant Geometry: | Cylinder | Cylinder | Cylinder | Wedge Shaped | Wedge Shaped | Rectangular Prism | Rectangular Prism |
| Polymer Used: | PEA | PEA | PEA | PLGA | PEA | PEA | PEA |
| Drug Present: | Yes | Yes | Yes | No | Yes | Yes | Yes |
| Nominal Dimension (μm): | 280D × 1500L | 280D × 1500L | 280D × 3000L | 210D × 225/200W × 2275L | 210D × 222/200W × 2350L | 220D × 220W × 2925L | 220D × 220W × 4500L |
| Interference Length (μm): | 0 | 0 | 0 | 481 | 489 | 2925 | 4500 |
| Measured Retention Dimension (μm): | 265 | 270 | 270 | 316 | 338 | 341 | 345 |
| Nominal Needle ID (μm): | 311 | 311 | 311 | 311 | 311 | 311 | 311 |

TABLE 1-continued

27G Ultra-thin

Needle Gauge: wall needle
Sample Group:

| | A | B | C | D | E | F1 | F2 |
|---|---|---|---|---|---|---|---|
| Ret Dim/Needle ID: | 0.85 | 0.87 | 0.87 | 1.02 | 1.09 | 1.10 | 1.11 |
| Retention Force (N) | | | | | | | |
| | 0.000 | 0.060 | 0.002 | 0.060 | 0.100 | 1.000 | 1.000 |
| | 0.002 | 0.000 | 0.012 | 0.090 | 0.158 | | |
| | 0.010 | 0.000 | 0.026 | 0.030 | 0.072 | | |
| | 0.012 | 0.042 | 0.024 | 0.040 | 0.058 | | |
| | 0.004 | 0.108 | 0.004 | 0.170 | 0.260 | | |
| | 0.010 | 0.006 | 0.010 | 0.080 | | | |
| | 0.002 | 0.000 | 0.006 | 0.050 | | | |
| | 0.006 | 0.004 | 0.000 | 0.080 | | | |
| | 0.000 | | 0.012 | | | | |
| | 0.000 | | 0.008 | | | | |
| | 0.000 | | 0.004 | | | | |
| | 0.000 | | | | | | |
| | 0.000 | | | | | | |
| | 0.018 | | | | | | |
| | 0.024 | | | | | | |
| | 0.022 | | | | | | |
| | 0.066 | | | | | | |

The test results show that the implant 100 of the present application (wedge shape) had the best retention force (over 0.350 lb) out of the seven different designs tested. The retention forces of the designs with uniform diameters were either too low (cylinder) and disengaged too easily, or too high (rectangular prism) and did not fit into the lumen of the needle.

In operation, the medical implant 100 is used in conjunction with a drug delivery device, such as a needle 200, to inject (insert) the medical implant 100 into a patient's tissue. In one example embodiment, the medical implant 100 is an intraocular lens implant configured to be injected into the posterior chamber of a patient's eye. First, the needle of the delivery device is inserted through the sclera of the posterior chamber. The implant(s) are then mechanically delivered into the posterior chamber by the forward motion of a pusher wire in the lumen of the needle, as shown in FIG. 5. The motion of the pusher wire may be driven by a variety of delivery device features, including metal or plastic springs or pneumatically. Actuation of this delivery mechanism may be accomplished by linking the delivery mechanism to a push button or slide on the device handle that is operated by the physician performing the procedure.

Figure 21:
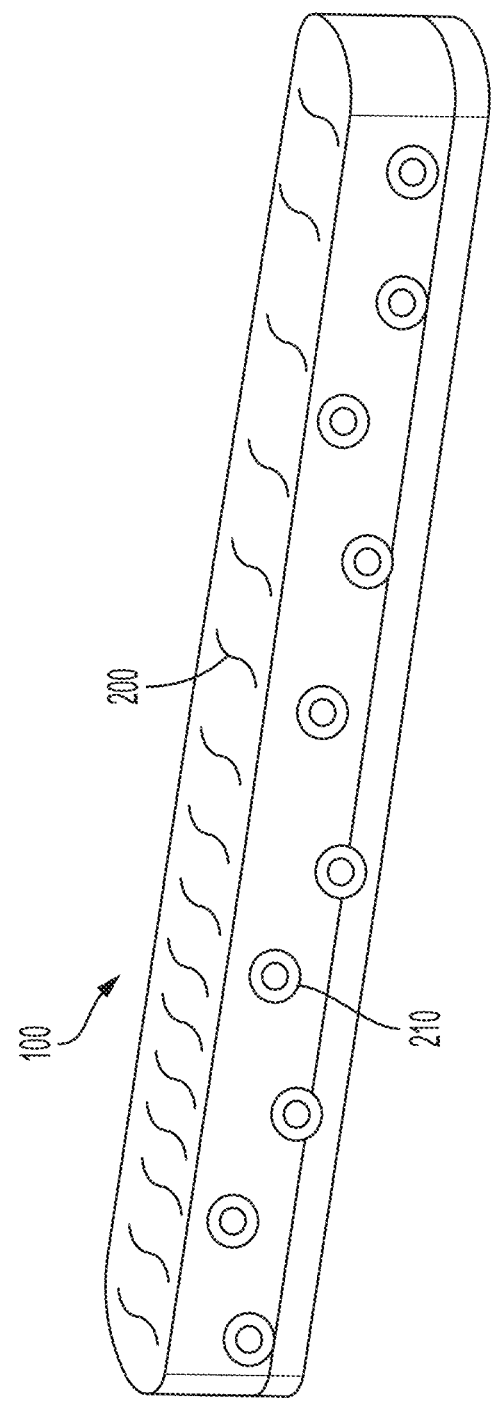
FIG. 21 is a perspective view of a medical implant having a surface modification.

Another aspect of the implants of the present disclosure is the ability to impart a surface modification (see FIGS. 21—200, 210) to create an interference surface of the medical implant 100. Such surface modification can enhance and optimize the retention force when the implant is loaded into a needle cannula. Examples of surface modifications can include coatings, films, biomatrices, nanostructures (nanotubes and nanopores), roughened, sputtered, and sprayed surfaces on both macro and nano scales. The rugosity or roughness of the implant surface could also be accomplished by including these texture features in the mold tools used to form the implants. Coatings and films could involve the use layering techniques applied to the surface of the implants, possibly using a combination of different polymers or other coating materials having different surface energies relative to the lumen of the contacted delivery device surfaces. Combinations of different surface modifications can also be used, for example, one type of surface modification 200 on one portion of the implant 100 and another surface modification 210 used on a different portion of the implant.

While a number of exemplary aspects and embodiments have been discussed above, those of skill in the art will recognize that still further modifications, permutations, additions and sub-combinations thereof of the features of the disclosed embodiments are still possible.

For the sake of clarity, the indefinite article "a" or "an" as used herein, and in the following claims, mean "one or more" and are to be construed in open-ended claims containing the transitional phrase "comprising" as meaning "at least one" or "one or more". Stated differently, the indefinite articles "a" or "an" should not be construed to mean only a single component, structure or element of the layered composite and method of making same.

The invention claimed is:

1. A layered composite containing a drug comprising: a substantially wedge shaped body having a width and a height; a tapered portion extending in a width direction between a first end and a second end, wherein the first end is configured to be initially retained in a cannula and the second end is configured to be inserted into an eye, wherein the first end has a first cross-section having a first cross-sectional dimension in a width direction and the second end has a second cross-section having a second cross-sectional dimension in the width direction, the first cross-sectional dimension being larger than the second cross-sectional dimension, wherein the tapered portion has a rectangular cross-section in the width direction, and wherein the height is substantially constant between the first end and the second end; a first layer comprising a first polymer; and a second layer comprising a first drug and a second polymer; wherein the first layer substantially covers the second layer and where a portion of the first layer defines a flat planar surface; wherein a retention force of the implant within the cannula is from about 0.030 N to about 0.260 N; and wherein a ratio of a diagonal dimension of the first cross-section, as a measured retention dimension, to an inside diameter of the cannula is between 1.0064 and 1.09 such that the body is configured to be inserted and removed from the cannula by a user for insertion of the body into an eye of a patient for medical treatment of the eye.

2. The layered composite of claim 1, wherein the first layer further comprises a second drug.

3. The layered composite of claim 2, wherein the second drug is the same as the first drug.

4. The layered composite of claim 1, wherein the first polymer is the same as the second polymer.

5. The layered composite of claim 1 further comprising a third layer, wherein the third layer surrounds the second layer and is press molded directly to the flat planar surface.

6. The layered composite of claim 1, wherein a length of the first end of the body to the tapered portion is less than 50% of the total length of the layered composite.

7. The layered composite of claim 1, wherein the first end and the second end each have a rounded profile.

8. The layered composite of claim 1, wherein the layered composite is manufactured using a particle replication in non-wetting templates (PRINT) method to form and shape the layered composite.

9. The layered composite of claim 5, wherein the layered composite is manufactured using a particle replication in non-wetting templates (PRINT) method to form and shape the layered composite.

10. The layered composite of claim 9, wherein a laminate structure is prepared prior to forming the layered composite using the PRINT method, where the laminate structure has a top, a middle and a bottom,
    wherein the first layer comprises a portion of the bottom, the second layer comprises a portion of the middle and the third layer comprises a portion of the top.

11. The layered composite of claim 10 configured as a medical implant and sized for insertion into tissue using a needle attached to a drug delivery device.

12. A layered composite containing a drug comprising: a substantially wedge shaped body having a width and a height; a tapered portion extending in a width direction between a first end and a second end, wherein the first end is configured to be initially retained in a cannula and the second end is configured to be inserted into an eye, wherein the first end has a first cross-section having a first cross-sectional dimension in a width direction and the second end has a second cross-section having a second cross-sectional dimension in the width direction, the first cross-sectional dimension being larger than the second cross-sectional dimension, and wherein the tapered portion has a rectangular cross-section in the width direction, and wherein the height is substantially constant between the first end and the second end; a first layer comprising a first polymer, where a portion of the first layer defines a flat planar surface; a second layer comprising a first drug and a second polymer; and a third layer, where the third layer surrounds the second layer and is press molded directly to the flat planar surface, and wherein the first layer and third layer have the same composition; wherein a retention force of the implant within the cannula is from about 0.030 N to about 0.260 N; and wherein a ratio of a diagonal dimension of the first cross-section, as a measured retention dimension, to an inside diameter of the cannula is between 1.0064 and 1.09 such that the body is configured to be inserted and removed from the cannula by a user for insertion of the body into an eye of a patient for medical treatment of the eye.

13. The layered composite of claim 12, wherein the first layer comprises a second drug.

14. The layered composite of claim 13, wherein the second drug is the same as the first drug.

15. The layered composite of claim 12, wherein a laminate structure comprising the first layer, the second layer and the third layer is used in a PRINT method to form the layered composite, where a top portion of the laminate structure forms the third layer, a middle portion of the laminate structure forms the second layer, and a bottom portion of the laminate structure forms the first layer.

16. The layered composite of claim 2, wherein the first and second polymers comprise body biocompatible polymers and the first and second drugs comprise a therapeutic or diagnostic agent.

* * * * *